United States Patent [19]

Yamamoto et al.

[11] Patent Number: 5,723,110
[45] Date of Patent: Mar. 3, 1998

[54] DEODORANT COSMETIC COMPOSITION SUPERIOR IN RESISTANCE TO DISCOLORATION AND DISPERSION

[75] Inventors: Tatsuo Yamamoto, Inazawa; Masashi Uchida; Yasuo Kurihara, both of Nagoya, all of Japan

[73] Assignee: Shinagawa Fuel Co., Ltd., Tokyo, Japan

[21] Appl. No.: 504,389

[22] Filed: Jul. 19, 1995

[30] Foreign Application Priority Data

Jul. 19, 1994 [JP] Japan ................................. 6-166926
Jun. 12, 1995 [JP] Japan ................................. 7-143775

[51] Int. Cl.$^6$ ........................ A61K 7/32; A61K 31/74; C01B 39/00
[52] U.S. Cl. .................... 424/65; 423/700; 424/66; 424/67; 424/68; 424/69; 424/78.08; 424/78.1; 424/400; 424/401; 424/617; 424/618; 424/630; 424/641; 424/684; 424/DIG. 5; 514/970
[58] Field of Search ...................... 424/65, 66, 67, 424/68, 400, 401, DIG. 5, 78.08, 78.1; 514/970; 423/700

[56] References Cited

U.S. PATENT DOCUMENTS

| | | | |
|---|---|---|---|
| 4,362,715 | 12/1982 | Strianse et al. | 424/78 |
| 4,938,958 | 7/1990 | Niira et al. | 424/79 |
| 5,211,870 | 5/1993 | Gilbert et al. | 252/120 |

FOREIGN PATENT DOCUMENTS

| | | |
|---|---|---|
| 60-178810 | 9/1985 | Japan. |
| 63-250325 | 10/1988 | Japan. |
| 63-265809 | 11/1988 | Japan. |
| 1-305013 | 12/1989 | Japan. |
| 5-163125 | 6/1993 | Japan. |
| 93/17661 | 9/1993 | WIPO. |

*Primary Examiner*—Shelley A. Dodson
*Attorney, Agent, or Firm*—Foley & Lardner

[57] ABSTRACT

The cosmetic composition is disclosed by blending at least an antibacterial zeolite, having all or part of its ion exchangeable ions substituted by ammonium ions and antibacterial metal ions, and silicone.

31 Claims, No Drawings

DEODORANT COSMETIC COMPOSITION SUPERIOR IN RESISTANCE TO DISCOLORATION AND DISPERSION

BACKGROUND OF THE INVENTION

1. Field of Invention

The present invention relates to a deodorant cosmetic composition superior in resistance to discoloration and dispersion.

2. Description of the Related Art

A deodorant cosmetic composition is a cosmetic composition used to prevent the dispersion or secretion of unpleasant body odors or to cancel but the dispersion or secretion. The product generally takes the form of lotion, a cream, powder, stick, or aerosol.

Body odor is mainly due to the decomposition of sweat. There are the following methods for preventing body odor occurring along with sweat.

A powerful astringent action is used to suppress the secretion of sweat and thereby indirectly prevent body odor. For example, zinc paraphenolsulfonate, citric acid, or various types of aluminum compounds or other astringents are often used. In addition, ethyl alcohol also has an astringent action. Among these, particularly aluminum compounds (aluminum hydroxychloride) is frequently used. For aerosol types, a complex with propylene glycol having good compatibility with chlorofluorocarbon gas has been developed.

Sweat breaks down and gives off an odor due to the decomposition action of bacteria. Bactericides are used to prevent the propagation of bacteria and thereby directly prevent the breakdown of sweat and the resultant odor. For example, TMTD (tetramethylthiuram disulfide), benzalkonium chloride, 3-trifluoromethyl-4,4'-dichloro carbonilide (halocarban), etc., are often used. In addition, zinc oxide, essential oils, perfumes, chlorophyll compounds, etc. have antibacterial actions.

Normal body odor can be sufficiently cancelled out by perfumes, eau de colognes, etc., and therefore, the above mentioned bactericides etc. are sometimes blended with these so as to indirectly promote the anti-odor effect. The purpose of use is substantially the same as with eau de colognes.

However, as antibacterial spray compositions using the bactericidal action among these actions, there have been known in the past, as disclosed in Japanese Unexamined Patent Publication (Kokai) No. 63-250325, an antibacterial spray composition including an antibacterial zeolite powder, alcohol, and a propellant. Here, the antibacterial zeolite is zeolite with a part or all of the ion exchangeable ions substituted by ammonium ions and antibacterial metal ions.

This deodorant cosmetic composition, however, has the problem of a feeling of roughness at the time of use. Further, a much more superior deodorizing effect is desired.

The antibacterial zeolite of the above disclosed art achieves the effect of enabling an extreme reduction of discoloration of resin products to which it is added. The present inventors tried blending antibacterial zeolite of the above disclosed art into a cosmetic composition. As a result, they found that while the resistance to discoloration was better than with cosmetic compositions into which other antibacterial zeolites had been blended, even so a somewhat large change in color was observed and therefore the results were not necessarily satisfactory in terms of the level demanded for a cosmetic composition.

SUMMARY OF THE INVENTION

Accordingly, the objects of the present invention are to eliminate the above-mentioned disadvantages of the prior art and to provide a deodorant cosmetic composition superior over the past in useability (i.e., no rough feeling) and further superior in deodorizing effect and resistance to discoloration.

In accordance with the present invention, there is provided a deodorant cosmetic composition superior in resistance to discoloration and dispersion comprising (i) an antibacterial zeolite having all or a part of its ion exchangeable ions substituted with ammonium ions and antibacterial metal ions, and (ii) silicone, blended together.

Mode of operation of the present invention will be explained, along with the discoveries etc. obtained at the time of completing the present invention.

The present inventors investigated in depth the causes for the rough feeling in the conventional deodorant cosmetic compositions described above. As a result, they discovered that the powder was not necessarily dispersed well in the substrate and, further, that the powder sometimes ending up aggregating. Further, they arrived at the idea that the poor dispersion and aggregation were the causes for the rough feeling and probably the causes for poor deodorizing effect.

Therefore, they investigated in depth the means for eliminating these causes.

The inventors engaged in repeated massive experiments and as a result discovered that when silicone is blended in, the deodorant cosmetic composition loses its rough feeling at the time of use and is improved in deodorizing effect.

Further, we found that the powder could be dispersed well, without causing aggregation (dispersion of powder at time of manufacturing in the case of a stick).

In addition, importantly, we found that while the antibacterial zeolite discussed in the above prior art was not necessarily satisfactory in terms of the resistance to discoloration when blended in a cosmetic composition by itself, the deodorant cosmetic composition was superior in resistance to discoloration when silicone was simultaneously blended in.

The present invention was made based on this finding. However, it is not clear why the roughness at the time of use disappears, the deodorizing effect becomes excellent, and the resistance to discoloration becomes much more superior when silicone is blended in.

Embodiments of the present invention will be explained below.

Antibacterial Zeolite

The antibacterial zeolite in the present invention is zeolite with a part or all of the ion exchangeable ions substituted by ammonium ions and antibacterial metal ions.

Here, the zeolite used may be any of a natural zeolite or artificial zeolite.

The zeolite is generally an aluminosilicate having a three-dimension framework and is expressed by the general formula $XM_{2/n}O.Al_2O_3.YSiO_2.ZH_2O$. Here, M indicates an ion exchangeable ion, normally a mono or divalent metal ion. n is the atomic value of the (metal) ion. X and Y are respectively a metal oxide and the silica coefficient, and Z is the number of water of crystallization.

Specific examples of the zeolite include, for example, Type A zeolite, Type X zeolite, Type Y zeolite, Type T zeolite, high silica zeolite, sodalite, mordenite, analcime, crynoptyrolite, chabazite, erionite, etc., although the zeolite usable in the present invention is not limited to these examples.

Note that the ion exchange capacity of the zeolites illustrated are 7 meq/g for Type A zeolite, 6.4 meq/g for Type X zeolite, 5 meq/g for Type Y zeolite, 3.4 meq/g for Type T zeolite, 11.5 meq/g for sodalite, 2.6 meq/g for mordenite, 5 meq/g for analcime, 2.6 meq/g for clinoptilolite, 5 meq/g for chabazite, and 3.8 meq/g for erionite, all capacities sufficient for ion exchange by ammonium ions and silver ions.

As the ion exchangeable ions in the zeolite, for example, mention may be made of sodium ions, calcium ions, potassium ions, magnesium ions, iron ions, etc.

As examples of the antibacterial metal ions, mention may be made of silver, copper, zinc, mercury, tin, lead, bismuth, cadmium, chromium, and thallium ions, preferably silver, copper, and zinc ions.

From the viewpoint of antibacterial property, the above antibacterial metal ions are preferably contained in the zeolite in an amount of 0.1 to 15% by weight. An antibacterial zeolite containing 0.1 to 15% of silver ions and 0.1 to 8% of copper ions or zinc ions is more preferable. On the other hand, ammonium ions may be included in the zeolite up to 20%, but from the viewpoint of the effective prevention of discoloration by the zeolite, 0.5 to 5% in the zeolite is more preferable and 0.5 to 2% even more preferable. Note that the percent figures here are percents by weight based on the dry weight at 110° C.

Method of Manufacture of Antibacterial Zeolite

The antibacterial zeolite of the present invention is prepared by bringing zeolite into contact with a mixed aqueous solution prepared in advance and containing ammonium ions and silver ions, copper ions, zinc ions, and other antibacterial metal ions and causing substitution between the ion exchangeable ions in the zeolite and the above ions. The contact can be performed at 10° to 70° C., preferably 40° to 60° C., for 3 to 24 hours, preferably 10 to 24 hours, by the batch or continuous (or column) method. Note that the pH of the above mixed aqueous solution is suitably adjusted to 3 to 10, preferably 5 to 7. This adjustment is preferable in that it is possible to prevent the precipitation of the silver oxides etc. on the zeolite surface or in the pores. Further, the ions in the mixed aqueous solution are normally all supplied as salts. For example, the ammonium ions used may be ammonium nitrate, ammonium sulfate, ammonium acetate, ammonium perchlorate, ammonium thiosulfate, and ammonium phosphate, the silver ions used may be silver nitrate, silver sulfate, silver perchlorate, silver acetate, diamminesilver nitric acid salt, diamminesilver sulfuric acid salt, etc., the copper ions used may be (II) copper nitrate, copper perchlorate, copper acetate, potassium tetracyanocuprate (or tetracyano cupric acid), copper sulfate, etc., the zinc ions used may be (II) zinc nitrate, zinc sulfate, zinc perchlorate, zinc thiocyanate, zinc acetate, etc., the mercury ions used may be mercury perchlorate, mercury nitrate, and mercury actate, the tin ions used may be tin sulfate etc., the lead ions used may be lead sulfate, lead nitrate, etc., the bismuth ions used may be bismuth chloride, bismuth iodide, etc., the cadmium ions may be cadmium perchlorate, cadmium sulfate, cadmium nitrate, and cadmium acetate, the chromium ions may be chromium perchlorate, chromium sulfate, ammonium chromium sulfate, chromium nitrate, etc., and the thallium ions used may be thallium perchlorate, thallium sulfate, thallium nitrate, thallium acetate, etc.

The content of the ammonium ions in the zeolite may be suitably controlled by adjusting the concentration of the ions (salts) in the above mixed aqueous solution. For example, when the antibacterial zeolite includes ammonium ions and silver ions, the concentration of ammonium ions in the above mixed aqueous solution may be made 0.2M/liter to 2.5M/liter and the concentration of silver ions may be made 0.002M/liter to 0.15M/liter so as to obtain an antibacterial zeolite with a suitable ammonium ion content of 0.5 to 5% and silver ion content of 0.1 to 5%. Further, when the antibacterial zeolite further contains copper ions and zinc ions, the concentration of copper ions in the above mixed aqueous solution may be made 0.1M/liter to 0.85M/liter and the concentration of zinc ions may be made 0.15M/liter to 1.2M/liter so as to obtain an antibacterial zeolite with a suitable copper ion content of 0.1 to 8% and zinc ion content of 0.1 to 8%.

In the present invention, in addition to the above described mixed aqueous solution, it is possible to perform ion exchange by using aqueous solutions containing these individual ions alone and successively causing contact between these aqueous solutions and the zeolite. The concentration of ions in the individual aqueous solutions may be determined in accordance with the concentrations of ions in the above mixed aqueous solution.

The zeolite finished with the ion exchange is fully rinsed, then dried. The drying is preferably performed at 105° C. to 115° C. or under reduced pressure (e.g., 1 to 30 Torr) at 70° C. to 90° C.

Note that the ion exchange by tin, bismuth, and other ions without suitable water soluble salts and organic ions may be performed by using alcohol, acetone, and other organic solvent solutions and causing reactions in a manner where the insoluble basic salts do not precipitate.

Amount of Antibacterial Zeolite Blended

The amount of the antibacterial zeolite blended in is preferably at least 0.1% by weight. When at least 0.1% by weight, the deodorizing effect appears much more remarkably.

Further, in the case of an aerosol type, that is, a spray type, when the amount is at least 1.0% by weight, the deodorizing effect is even further improved, so this is even more preferable. When over 70% by weight, the amount of the powder component is larger than that of the oily component, the feeling when used becomes poor. Thus, the amount of 70% by weight or less is preferable.

In the case of a stick type, when the amount is at least 5.0% by weight, the deodorizing effect is further improved, and therefore, this is preferable. When over 70% by weight, however, the molding into a stick shape becomes difficult, and therefore, an amount of 70% by weight or less is more preferable.

In the case of a powder type or pressed powder (powder molding type), when the amount is at least 5.0% by weight, the deodorizing effect is even further improved, and therefore this is more preferable. When over 99.9% by weight, however, the feeling when used becomes powder-like feeling.

In the case of a lotion type, when the amount is at least 5.0% by weight, the deodorizing effect is further improved, and therefore, this is more preferable. When over 20% by weight, however, the dispersion of the powder component in the liquid phase, and therefore, 20% by weight or less is more preferable.

Particle Size of Antibacterial Zeolite

The particle size of the antibacterial zeolite is preferably not more than an average particle size of 10.0 µm. Further, it is preferable when the range of particle sizes be such that particles which exceed 10 μm are not more than 20% of the total antibacterial zeolite. When the average particle size exceeds 10 μm or when the range of particle sizes exceeds 10 μm, the dispersion in the deodorant cosmetic composition becomes worse and a rough feeling is given at the time of use in some cases.

Silicone

The silicone blended in the present invention may be silicone oil or volatile silicone, or both the silicone oil and the volatile silicone may also be blended simultaneously.

Examples of the silicone oil include, for example, dimethyl polysiloxanes expressed by
$(CH_3)_3SiO[(CH_3)_2SiO]_n(CH_3)_3$ (wherein, n is 3 to 650),
$(CH_3)_3SiO[(CH_3)_2SiO]_n[(C_6H_5)_2SiO]_mSi(CH_3)_3$ (wherein, n is an integer of from 1 to 500), $(CH_3)_3SiO[(CH_3)_2SiO]_n[(CH_3)(C_6H_5)SiO]_mSi(CH_3)_3$ (wherein, n and m are integers of from 1 to 500),
$(CH_3)_3SiO[(CH_3)(C_6H_5)SiO]_n[(C_6H_5)_2SiO]_mSi(CH_3)_3$ (wherein, n and m are integers of from 1 to 500),
and a methylphenyl polysiloxane expressed by the general formula (1) (wherein, n and m are integers of from 1 to 500).

When using a dimethyl polysiloxane and a methylphenyl polysiloxane (wherein, n and m are integers of from 1 to 500), the resistance to discoloration is particularly superior compared with the case of using other silicones.

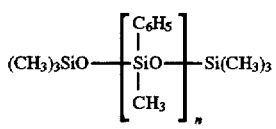

As the dimethyl polysiloxane, one with a viscosity of 0.65 to 5,000 cst at 25° C. is particularly preferable from the viewpoint of practical use. Further, as the methylphenyl polysiloxane, one with a viscosity of 10 to 1000 cst at 25° C. is particularly preferable from the viewpoint of practical use.

Examples of the volatile silicone include, dimethyl polysiloxanes expressed by
$(CH_3)_3SiO[(CH_3)_2SiO]_n(CH_3)_3$ (wherein, n is an integer of from 0 to 5),
a cyclic dimethyl polysiloxane expressed by the general formula (2) (wherein, n is an integer of from 3 to 7), etc.

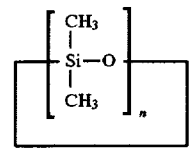

As the cyclic dimethyl polysiloxane, octamethylcyclotetrasiloxane, decamethylcyclopentasiloxane, and dodecamethylcyclohexanesiloxane are particularly preferable.

Further, a polyoxyethylene-modified organopolysiloxane may also be used.

Examples of the polyoxyethylene-modified organopolysiloxane, include those having the following general formulas (3) to (5). At least one of these compounds may be used.

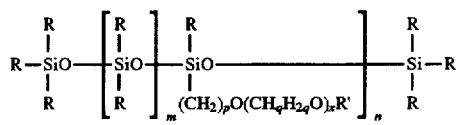

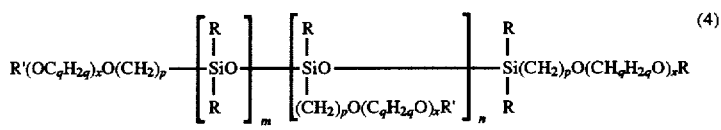

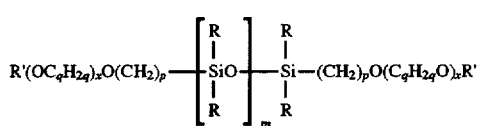

(in general formulae (3), (4), and (5), R is a methyl group or partially a phenyl group, R' is a hydrogen atom or an alkyl group having 1 to 12 carbon atoms, p is 1 to 5, q is an integer of 2 to 3, and x, m, and n are averages whereby the polyoxyalkylene modified organopolysiloxane will contain 2 to 90% by weight of polyoxyalkylene groups in the molecule and the viscosity of the polyoxyalkylene modified organopolysiloxane will be 5 to 5000 centipoises at 25° C.).

Other silicones are as follows:

A high molecular weight silicone expressed by the formula (6)

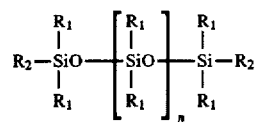

(wherein, $R_1$ is a methyl group or phenyl group (however, excluding cases where the $R_1$ are all phenyl groups), and $R_2$ is a methyl group or hydroxyl group. Further, n is an integer of from 3000 to 20,000).

An organic silicone resin comprised of units of the average formula $RnSiO_{(4-n)/2}$ (where R is a hydrocarbon group of 1 to 6 carbon atoms or a phenyl group and n is a value of from 1.0 to 1.8).

Amount of Silicone Blended

Silicone improves the resistance to discoloration when blended in an amount of at least 0.01% by weight. The ratio of weight with the antibacterial zeolite, however, is important. It is preferable to blend in an amount of silicone at least 1/10 the weight of the antibacterial zeolite. When at least 1/10, the resistance to discoloration and effect of prevention of aggregation of the powder become more remarkable and, further, the practical use and deodorizing effect are also much more improved. The fact that the properties change due to the ratio between the amount of the antibacterial zeolite blended and the amount of the silicone blended in this way is believed to be due to the fact that the silicone and antibacterial zeolite interact in some way to bring about the effects.

Note that the upper limit on the amount of the silicone blended is 80% by weight in the case of an aerosol type, stick, or lotion. When exceeding 80% by weight, the feeling when use is not preferable because of stickiness and oiliness.

In the case of a powder, the upper limit of the amount of the silicone is 10% by weight. When exceeding 10% by weight, the powder component is leaked, whereby the feelings when use become heavy and further when the silicone amount becomes large, the slurry is formed and the powder form cannot be maintained.

Further, the deodorant cosmetic composition of the present invention may be obtained by uniformly mixing the antibacterial zeolite and silicone at the time of manufacture by a method normally used for manufacturing deodorant cosmetic compositions and cosmetic compositions. Further, it is possible to use surface treated antibacterial zeolite obtained by treating (causing absorption by) the surface of the antibacterial zeolite in advance with a silicone able to be blended in the present invention and possible to combine silicone with this.

Aluminum Compounds

In the present invention, selective blending of aluminum compounds is preferable in the sense of further enhancing the deodorizing effect caused by enhancing the sweat suppressing effect.

In the present invention, as the aluminum compounds, suitable use may be made for example of the following:

Aluminum chloride, aluminium chlorohydroxy allantoinate, aluminum sulfate, alum, aluminum hydroxychloride, aluminium dihydroxy allantoinate, aluminum zirconium chlorohydrates and its derivatives, aluminum zirconium organic complex salts (for example, aluminum zirconium tetrachlorohydrex gly, zirconium aluminum glycine hydroxychloride complex).

Among these, aluminum hydroxychloride is the most preferable.

Metal Oxides

Metal oxides are preferably blended in from the viewpoint of enhancing the odor-cancelling effect.

As metal oxides preferably blended in the present invention, mention may be made for example of zinc oxide, magnesium oxide, calcium oxide, etc. Magnesium oxide is preferable and zinc oxide is most preferable.

Other Optional Components

As other optical components, it is possible to blend the following:

1. Powder Components (1) Inorganic Powders

Talc, kaolin, silica, mica, sericite, dolomite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, tungstic acid metal salts, magnesium, silica, zeolite, barium sulfate, sintered calcium sulfate, (sintered gypsum), calcium phosphate, fluoroapatite, hydroxyapatite, ceramic powder, metal soap (zinc myristate, calcium palmitate, aluminum stearate), boron nitride, etc.

(2) Organic Powders

Polyamide resin powders (nylon powders), polyethylene powder, polymethyl methacrylate powder, polystyrene powder, styrene-acrylate copolymer resin powder, benzoguanamine resin powder, polytetrafluoroethylene powder, cellulose powder, calcium alginate powder, etc.

(3) Inorganic Pigments (4) Organic Pigments (5) Dyes (6) Natural Colors

2. Oil Components (1) Oils and Fats (Liquid Oils and Fats)

Avocado oil, tsubaki oil, macademia nut oil, corn oil, mink oil, olive oil, rapeseed oil, eggyolk oil, sesame oil, wheat germ oil, castor oil, flaxseed oil, safflower oil, cottonseed oil, soybean oil, peanut oil, tea seed oil, rice bran oil, jojoba oil, germ oil, triglycerine oil, glyceryl trioctanoute, glycerol triisopalmitate, etc.

(2) Oils and Fats (Solid Oils and Fats)

Cacao oil, coconut oil, horse fat, hardened castor oil, palm oil, beef tallow, sheep tallow, hardened beef tallow, palmnut oil, pork tallow, beef bone fat, Japan wax nut oil, hardened oil, beef foot oil, Japan wax, hardened castor oil, etc.

(3) Waxes

Beeswax, candellia wax, cotton wax, carnauba wax, bayberry wax, insect wax, spermaceti, montan wax, rice bran wax, lanolin, kapok wax, lanolin acetate, liquid lanolin, sugar cane wax, isopropyl lanolin fatty acid, hexyl laurate, reduced lanolin, jojoba wax, hydrogenated lanolin, shellac wax, POE lanolin alcohol ether, POE lanolin alcohol acetate, POE cholesterol ether, polyethylene glycol lanolin fatty acid, POE hydrated lanolin alcohol ether, etc.

(4) Hydrocarbons

Liquid paraffin, ozokerite, squalane, pristane, paraffin, ceresine, squalane, vaseline, microcrystalline wax, etc.

3. Higher Aliphatic Acids

Lauric acid, myristic acid, palmitic acid, stearic acid, behenic acid, oleic acid, 12-hydroxystearic acid, undecylic acid, tollic acid, isostearic acid, lanolic acid, lanolenic acid, eicosapentaenoic acid (EPA), docosahexanoic acid (DHA), etc.

4. Higher Alcohols (1) Straight Chain Alcohols

Lauryl alcohol, cetyl alcohol, stearyl alcohol, behenyl alcohol, myristyl alcohol, oleic alcohol, cetostearyl alcohol, etc.

(2) Branched Chain Alcohols

Monostearylglycerine ether (vatyl alcohol), 2-decyltetradecynol, lanolin alcohol, cholesterol, phytosterol, hexydodecanol, isostearyl alcohol, octyl dedecanol, etc.

5. Esters

Isopropyl myristate, cetyl octanate, octyldodecyl myristate, isopropyl palmitate, butyl stearate, hexyl laurate, myristyl myristate, decyl oleate, hexyldecyl dimethyloctanate, cetyl lactate, myristyl lactate, lanolin acetate, isocetyl stearate, isocetyl isostearate, cholesteryl 12-hydroxystearate, ethylene glycol 2-ethylhexylate, dipentaerysterol fatty acid ester, N-alkylglycol monoisostearate, neopentylglycol dicaprate, diisostearyl malate, glycerol di-2-heptyl undecanate, trimethylolpropane tri-2-ethylhexylate, trimethylolpropane triisostearate, pentanerysterol tetra-2-ethylhexylate, glycerol tri-2-ethylhexylate, trimethylolpropane triisostearate, cetyl 2-ethylhexanoate, 2-ethylhexylpalmitate, glycerol trimyristate, glyceride tri-2-heptylundecanoate, methyl ester of castor oil fatty acid, oleic acid oil, cetostearyl alcohol, acetoglyceride, 2-heptylundecyl palmitate, diisobutyl adipate, di-(2-octyldodecyl)N-lauryl-L-glutamate, di-2-heptylundecyl adipate, ethyl laurate, di-2-ethylhexyl sebacate, 2-hexyldecyl myristate, 2-hexyldecyl palmitate, 2-hexadecyl adipate, diisopropyl sebacate, 2-ethylhexyl succinate, ethyl acetate, butyl acetate, amyl acetate, triethyl citrate, etc.

6. Anionic Surfactants (1) Fatty Acid Soap

Soap base, sodium laurate, sodium palmitate, etc.

(2) Higher Alkyl Sulfuric Acid Ester Salts

Sodium lauryl sulfate, potassium lauryl sulfate, etc.

(3) Triethanolamine Polyoxyethylene Lauryl Ether Sulfate

Sodium polyoxyethylene lauryl ether sulfate, etc.

(4) N-Acylsarcosine Acid Salts

Sodium lauryol sarcosine etc.

(5) Higher Fatty Acid Amide Sulfonic Acid Salts

Sodium N-myristoyl-N-methyltaurine, sodium coconut oil fatty acid methyltaurine, sodium laurylmethyltaurine, etc.

(6) Sodium Phosphoric Acid Ether, Polyoxyethylene Oleyl Ether Phosphate, Sodium Polyoxyethylene Stearyl Ether Phosphate, Etc.

(7) Sulfosuccinic Acid Salts

Sodium di-2-ethylhexylsulfosuccinate, sodium monolauroylmonoethanolamide polyoxyethylene-sulfosuccinate, sodium lauryl polypropylene glycolsulfosuccinate, etc.

(8) Alkylbenzenesulfonic Acid Salts

Sodium dodecylbenzene sulfonate, triethanolamine dodecylbenzene sulfonate, dodecylbenzene sulfonate, etc.

(9) N-acylglutamic Acid Salts

Monosodium N-lauroylglutamate, disodium N-stearoylglutamate, monosodium N-myristoyl-L-glutamate, etc.

(10) Higher Fatty Acid Ester Sulfuric Acid Ester Salts

Sodium hydrogenerated glyceryl cocoate sulfate etc.

(11) POE Alkylether Carboxylic Acid Salts

(12) POE Alkyl Allylether Carboxylic Acid Salts

(13) α-Olefin Sulfonic Acid Salts

(14) Higher Fatty Acid Ester Sulfonic Acid Salts

(15) Secondary Alcohol Sulfuric Acid Ester Salts

(16) Higher Fatty Acid Alkylolamide Sulfuric Acid Ester Salts

(17) Others

Sodium lauroylmonoethanolamide succinate, ditriethanolamine N-palmitoylasparate, sodium casein, etc.

7. Cationic Surfactants (1) Alkyltrimethylammonium Salts

Stearyltrimethylammonium chloride, lauryltrimethylammonium chloride, etc.

(2) Dialkyldimethylammonium Salts

Distearyldimethylammonium chloride etc.

(3) Alkyl Pyridinium Salts

Poly(N,N'-dimethyl-3,5-methylenepiperidinium) chloride, cetylpyridinium chloride, etc.

(4) Alkyl Quaternary Ammonium Salts (5) Alkyl Dimethylbenzyl Ammonium Salts (6) Alkyl Isoquinolinium Salts (7) Dialkyl Morihonium Salts (8) POE Alkyl Amines (9) Alkyl Amine Salts

(10) Polyamine Fatty Acid Derivatives

(11) Amyl Alcohol Fatty Acid Derivatives

(12) Quaternary Ammonium Salts

Benzalkonium chloride, benztonium chloride, etc.

8. Amphoteric Surfactants

Amidobetaine amphoteric surfactants, amidosulfobetaine amphoteric surfactants, betaine amphoteric surfactants, sulfobetaine amphoteric surfactants, imidazolinium amphoteric surfactants, etc.

9. Anionic Surfactants (1) Lyophilic Anionic Surfactants a. Sorbitan fatty acid esters Sorbitan monooleate, sorbitan monoisostearate, sorbitan monolaurate, sorbitan monopalmitate, sorbitan monostearate, sorbitan sesquioleate, diglycerol sorbitan trioleate, sorbitan penta-2-ethylhexylate, diglycerol sorbitan tetra-2-ethylhexylate, etc.

b. Glycerol or polyglycerol fatty acids

Glycerol monocottonseed oil fatty acid, glycerol monoerucate, glycerol sesquioleate, glycerol monostearate, diglycerol monostearate, glycerol α, glyceryl monopyroglutamate monooleate, glyceryl monostearate malate, etc.

c. Propylene glycol fatty acid esters

Propylene glycol monostearate, propylene glycol monolaurate, etc.

d. Hydrogenated castor oil derivatives e. Glycerol alkyl ethers (2) Hydrophilic Anionic Surfactants a. POE sorbitan fatty acid esters POE sorbitan monooleate, POE sorbitan monostearate, POE sorbitan monolaurate, POE sorbitan tetraoleate, etc.

b. POE sorbitol fatty acid esters

POE sorbitol monolaurate, POE sorbitol monooleate, POE sorbitol pentaoleate, POE sorbitol monostearate, etc.

c. POE glycerol fatty acid esters

POE glycerol monostearate, POE glycerol monoisostearate, POE glycerol triisostearate, etc.

d. POE fatty acid esters

POE monooleate, POE distearate, POE monodioleate, polyethylene glycol isostearate, etc.

e. POE alkyl ethers

POE lauryl ether, POE oleyl ether, POE stearyl ether, POE behenyl ether, POE octyl dodecyl ether, POE cholestanol ester, etc.

f. POE alkylphenyl ethers

POE octylphenyl ether, POE nonylphenyl ether, POE dinylphenyl ether, etc.

g. POE, POP alkyl esters

POE-POP cetyl ether, POE-POP 2-decyltetradecyl ether, POE,POP monobutyl ether, POE,POP hydrated lanolin, POE-POP glycerol ether, etc.

h. Tetra POE tetra POP ethylene diamine condensation products i. POE castor oil or hardened castor oil derivatives POE castor oil, POE hardened castor oil, POE hardened castor oil monoisostearate, POE hardened castor oil triisostearate, POE hardened castor oil monopyroglutamic acid monoisostearic acid diester, POE hardened castor oil malic acid, etc.

j. POE beeswax lanolin derivative
POE sorbitol beeswax etc.

k. Alkanolamides

Coconut oil fatty acid diethanol amide, lauric acid monoethanol amide, fatty acid isopropanol amide, etc.

l. POE propylene glycol fatty acid ester m. POE alkyl amine n. POE fatty acid amide o. Sucrose fatty acid ester 10. UV Absorbants (1) Benzoic Acid Type UV Absorbants p-Aminobenzoic acid (hereinafter referred to as "PABA"), PABA monoglycerine esters, N,N'-dipropoxy PABA ethyl ester, N,N'-diethoxy PABA ethyl esters, N,N'-dimethyl PABA ethyl esters, N,N'-dimethyl PABA butyl esters, N,N'-dimethyl PABA ethyl esters, etc.

(2) Anthranilic Acid Type UV Absorbants

Homomenthyl-N-acetylanthranilate etc.

(3) Salicylic Acid Type UV Absorbants

Amyl salicylate, menthyl salicylate, homomenthyl salicylate, octyl salicylate, phenyl salicylate, benzyl salicylate, p-isopropanolphenyl salicylate, etc.

(4) Cinnamic Acid Type UV Absorbants

Octyl cinnamate, ethyl-4-isopropyl cinnamate, methyl-2-5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glycerylmono-2-ethylhexanoyl-diparamethoxy cinnamate, etc.

(5) Benzophenone Type UV Absorbants 2,4-dihydroxy benzophenone, 2,2-dihydroxy-4-methoxy benzophenone, 2,2-dihydroxy-4,4'-dimethoxy benzophenone, 2,2,4,4-tetrahydroxy benzophenone, 2-hydroxy-4-methoxy benzophenone, 2-hydroxy-4-methoxy-4-methyl benzophenone, 2-hydroxy-4-methoxy benzophenone-5-sulfonic acid salts, 4-phenyl benzophenone, 2-ethylhexyl-4-phenyl-benzophenone-2-carboxylate, 2-hydroxy-4-n-octoxy benzophenone, 4-hydroxy-3-carboxy benzophenone, etc.

(6) Others 3-(4'-methylbenzylidene)-d,1-camphor, 3-benzylidene-d,1-camphor, urocanic acid, carocanic acid, ethyl ester, 2-phenyl-5-methylbenzoxazole, 2,2-hydroxy-5-methylphenylbenzotriazole, 2-(2'-hydroxy-5-t-octylphenyl)benzotriazole, 2-(2'-hydroxy-5'-t-octylphenyl)benzotriazole, 2-(2'-hydroxy-5'(methylphenylbenzotriazole, dibenzalazine, dianisylmethane, 4-methoxy-4'-t-butyldibenzoylmethane, 5-(3,3-dimethyl-2-norbornilidene)-3-pentane-2-on, etc.

11. Bactericides

Hinokitiol, chlorohexidine hydrochloride, phenoxy ethanol, hexachlorophene, 2,4,4'-trichloro-2'-hydroxydiphenylether (triclosan), vitionol, 3,4,4' trichlorocarbanilide (TCC), benzalkonium chloride, chlorobexidine hydrochloride, photosensitizer 201, photosensitizer 101, 1-hydroxypyridine-2-thion (zinc pyrithione), thiram (tetramethyl chivramdisulfide), halocarban, salicylic acid, etc.

Form

Examples of the forms of the deodorant cosmetic composition of the present invention are, for example, a spray type, roll-on type, powder type, pressed powder type, and stick type.

In the case of a spray type, the product is obtained by storing the cosmetic composition in a spray container along with liquified petroleum gas or other propellants and alcohol.

In the case of a roll-on type, the product is obtained by storing the cosmetic composition in a roll-on container along with alcohol.

In the case of a powder type and a pressed powder type, the product is obtained by mixing the cosmetic composition with a powder component and oil component. In the case of a powder type, this is then used as it is, while in the case of a pressed powder type, this is then shaped by various press machines.

In the case of a stick type, the product is obtained by mixing the cosmetic composition with an oil component (solid oil component and liquid oil component) and then filling the result in a container to shape it.

EXAMPLES

Examples 1 to 16 and Comparative Examples 1 to 3

Deodorant Powder Spray

Deodorant powder sprays were produced by the following manufacturing process in the compositions of Examples 1 to 16 and Comparative Examples 1 to 3 shown in Table 1. The redispersion of the powder and the useability (lack of roughness), deodorizing (underarm odor and foot odor) effect and resistance to discoloration were evaluated by the following methods. The results of evaluation are shown together in Table 1.

Manufacturing Process

The powder portion was mixed by a kneader, the oil component and dispersant were mixed by a blender, the powder portion and the oil component and dispersant were successively filled in an aerosol use glass container, then a propellant was filled to obtain a deodorant powder spray.

Method of Evaluation (1) Evaluation of Dispersion of Powder

This test is one of the methods for evaluation whether an aerosol product in which a powder is mixed can maintain its performance as a product.

The obtained aerosol was allowed to stand at 35° C. for one month.

The sample for evaluation was held in one hand and was shaken up and down at an amplitude of about 15 cm at a rate of two times a second. The number of shakings until all of the powder which had precipitated at the bottom of the glass bottle was dispersed was measured.

The smaller the number of shakes, the smaller the aggregation and solidification of the powder and the better the product.

⊙: Less than 10 times
o: 11 to 15 times
Δ: 16 to 20 times
×: 21 times or more (2) Aerosol (Test of Useability)

The following test was performed using a deodorant powder spray which had been allowed to stand for six months at room temperature.

Twenty test subjects sprayed the powders of the examples and comparative examples on one of their left and right armpits from a distance of 10 cm for 3 seconds. They then ran their hands over the applied samples and made organoleptic evaluations of the feeling of use on their own.

* Rough feeling is due to aggregation of powder.
(Criterion of Evaluation)
⊙: 18 to 20 subjects obtained non-rough feeling
o: 15 to 17 subjects obtained non-rough feeling
Δ: 10 to 14 subjects obtained non-rough feeling
×: 5 to 9 Subjects obtained non-rough feeling
××: 0 to 4 subjects obtained non-rough feeling (3) Test of Deodorizing Effect (Underarm Odor)

In this method, during the summer season, when people easily sweat, use was made of a panel of 20 male subjects conscious about underarm odor. An organoleptic evaluation was made by judges.

The test was performed by the double blind test method where test samples were allocated at random for the left and right and a person other than the panelists and judges allocated the samples and kept the key codes.

The armpits of the panelists were wiped with 70% ethanol until the underarm odor disappeared, then the samples were applied from a distance of 10 cm over 3 seconds. Each panelist was forbidden from taking a bath, using a shower, or washing his underarm. After 24 hours, the judges evaluated the degree of odor of the left and right armpits of the panelists by the following criteria:

Test of Deodorizing Effect: Criteria of Evaluation

The evaluation was made by judgement by the five-point method according to the following criteria. The results are shown using the average values of the results of judgement for the 20 male panelists. The higher the figures, the stronger the odor.

⊙: 0 to less than 1 point
o: 1 to less than 2 points
Δ: 2 to less than 3 points
×: 3 points or more (4) Test of Deodorizing Effect (Foot Odor)

In this method, during the summer season, when people easily sweat, use was made of a panel of 20 male subjects conscious about foot odor. An organoleptic evaluation was made of the foot odor by the test subjects by themselves.

The test was performed by the blind test method where test samples were allocated at random for the left and right and a person other than the test subjects allocated the samples and kept the key codes.

The feet of the test subjects were washed by a cosmetic composition soap until the foot odor disappeared, then the samples were applied by spraying from a distance of 5 cm from the feet for 3 seconds so as to deposit the powder sufficiently even between the toes.

Each panelist was forbidden from taking a bath, using a shower, or washing his feet. After 24 hours, the test subjects evaluated the degree of odor of the left and right feet by the same criteria as with the underarm odor:

(5) Test of Resistance to Discoloration

The powder portion before filling in the aerosol container was dried outdoors for 3 hours under the sunlight. The samples were placed on a white sheet of paper and evaluated visually by expert researchers as to whether a change of color had occurred compared with no irradiation by sunlight.

Note that the criteria of evaluation were as follows:
⊙: No change of color at all felt
o: Slight change of color felt
Δ: Somewhat large change of color felt
×: Large change of color felt

TABLE 1

| Composition | Example 1 | 2 | 3 | 4 | 5 | 6 | 7 | 8 | 9 | 10 |
|---|---|---|---|---|---|---|---|---|---|---|
| A | 0.05 | 0.1 | 5.0 | 10.0 | 30.0 | 3.0 | 3.0 | 3.0 | 3.0 | 3.0 |
| B | — | — | — | — | — | — | — | — | — | — |
| C | — | — | — | — | — | — | — | — | — | — |
| D | — | — | — | — | — | — | — | — | — | — |
| E | 0.5 | 0.5 | 0.5 | 0.5 | 0.5 | 0.5 | 0.5 | 0.5 | 0.5 | 0.5 |
| F | 0.5 | 0.5 | 0.5 | 0.5 | 0.5 | 0.5 | 0.5 | 0.5 | 0.5 | 0.5 |
| G | 3.0 | 3.0 | 3.0 | 3.0 | 3.0 | 0.1 | — | — | 1.5 | 1.5 |
| H | — | — | — | — | — | — | 3.0 | — | 1.5 | — |
| I | — | — | — | — | — | — | — | 3.0 | — | 1.5 |
| J | — | — | — | — | — | — | — | — | — | — |
| K | 0.1 | 0.1 | 0.1 | 0.1 | 0.1 | 0.1 | 0.1 | 0.1 | 0.1 | 0.1 |
| L | 10.0 | 10.0 | 10.0 | 10.0 | 10.0 | 10.0 | 10.0 | 10.0 | 10.0 | 10.0 |
| M | 85.85 | 85.8 | 80.9 | 75.9 | 55.9 | 85.8 | 82.9 | 82.9 | 82.9 | 82.9 |
| (1) | o | o | o | o | o | Δ | o | o | ⊙ | ⊙ |
| (2) | ⊙ | ⊙ | ⊙ | ⊙ | ⊙ | o | ⊙ | ⊙ | ⊙ | ⊙ |
| (3) | × | o | o | o | o | Δ | o | o | ⊙ | ⊙ |
| (4) | × | o | o | o | o | Δ | o | o | ⊙ | ⊙ |
| (5) | ⊙ | ⊙ | ⊙ | ⊙ | ⊙ | ⊙ | ⊙ | ⊙ | ⊙ | ⊙ |

| Composition | Example 11 | 12 | 13 | 14 | 15 | 16 | Comparative Example 1 | 2 | 3 |
|---|---|---|---|---|---|---|---|---|---|
| A | 3.0 | 3.0 | 3.0 | 3.0 | 3.0 | 3.0 | 3.0 | 3.0 | — |
| B | — | — | — | — | — | — | — | — | 3.0 |
| C | — | 2.0 | 2.0 | — | — | 1.0 | — | — | — |
| D | — | — | — | 2.0 | 2.0 | 1.0 | — | — | — |

TABLE 1-continued

| E | 0.5 | 0.5 | 0.5 | 0.5 | 0.5 | 0.5 | 0.5 | 0.5 | 0.5 |
|---|---|---|---|---|---|---|---|---|---|
| F | 0.5 | 0.5 | 0.5 | 0.5 | 0.5 | 0.5 | 0.5 | 0.5 | 0.5 |
| G | — | 3.0 | 1.5 | 3.0 | 1.5 | 1.5 | — | — | 3.0 |
| H | 1.5 | — | 1.5 | — | — | 1.5 | — | — | — |
| I | 1.5 | — | — | — | 1.5 | — | — | — | — |
| J | — | — | — | — | — | — | — | 3.0 | — |
| K | 0.1 | 0.1 | 0.1 | 0.1 | 0.1 | 0.1 | 0.1 | 0.1 | 0.1 |
| L | 10.0 | 10.0 | 10.0 | 10.0 | 10.0 | 10.0 | 10.0 | 10.0 | 10.0 |
| M | 82.9 | 80.9 | 80.9 | 80.9 | 80.9 | 85.9 | 82.9 | 82.9 | |
| (1) | ⊚ | ○ | ⊚ | ○ | ⊚ | ⊚ | x | x | ○ |
| (2) | ⊚ | ⊚ | ⊚ | ⊚ | ⊚ | ⊚ | Δ | x | ⊚ |
| (3) | ⊚ | ⊚ | ⊚ | ⊚ | ⊚ | ⊚ | Δ | Δ | Δ |
| (4) | ⊚ | ⊚ | ⊚ | ⊚ | ⊚ | ⊚ | Δ | Δ | Δ |
| (5) | ⊚ | ⊚ | ⊚ | ⊚ | ⊚ | ⊚ | Δ | Δ | Δ | wherein, in Table 1,

Powder Portion

A: Silver ion, zinc ion, and ammonium ion carrying zeolite (Zeomic AJ10N made by Shinanen Zeomic, average particle size about 1.5 μm)
B: Silver ion and zinc ion carrying zeolite (average particle size about 1.5 μm)
C: Aluminum hydroxychloride
D: Zinc oxide
E: Spherical silica
F: Talc Oil Component G: Dimethylpolysiloxane (6 cs)
H: Octamethyltetracyclosiloxane
I: Polyether modified dimethyl polysiloxane (POE content 15%, viscosity 400 cst/25° C.)
J: Isopropyl myristate Dispersant K: Polyoxyethylene sorbitan monooleate Propellant L: Isopentane
M: Liquified petroleum gas (1): Test of dispersion in powder
(2): Useability (lack of roughness)
(3): Odor (underarm odor)
(4): Odor (foot odor)
(5): Resistance to discoloration As will be understood from the above Examples and comparative examples, the deodorant powder sprays of the present invention are superior to the comparative examples in dispersion of the powder, useability, deodorizing effect, and resistance to discoloration.

Further, it is clear that when combining two or more types of silicones and by further adding a sweat suppressing component or an odor cancelling component, the dispersion of the powder, the useability, and the deodorizing effect become further superior.

Examples 17 to 29 and Comparative Examples 4 to 6

Deodorant Body Powders

The deodorant body powders of Examples 17 to 29 and Comparative Examples 4 to 6 shown in Table 2 were prepared and evaluated for useability (free from roughness), deodorizing effect (underarm odor and foot odor), and resistance to discoloration. The results are shown.

Manufacturing Process

The following components were successively mixed by a Henschel mixer to obtain the deodorant body powders.

Method of Evaluation (1) Useability

The deodorant powder was placed in a prescribed amount in a plastic container (non-hermetic) with a lid and stored under humid conditions (35° C., humidity 90%) for one month.

Twenty test subjects used the examples and comparative examples on either their left or right armpits using a special buff. They evaluated the feeling of use organoleptically on their own.

Criterion of Evaluation

⊚: 18 to 20 subjects obtained non-rough feeling
○: 15 to 17 subjects obtained non-rough feeling
Δ: 10 to 14 subjects obtained non-rough feeling
×: 5 to 9 subjects obtained non-rough feeling
××: 0 to 4 subjects obtained non-rough feeling The (2) deodorizing effect (underarm odor), (3) deodorizing effect (foot odor), and the (4) resistance to discoloration were performed the same way as with Examples 1 to 16.

TABLE 2

| | Example | | | | | | | | | |
|---|---|---|---|---|---|---|---|---|---|---|
| Composition | 17 | 18 | 19 | 20 | 21 | 22 | 23 | 24 | 25 | 26 |
| A' | 0.05 | 0.1 | 5.0 | 10.0 | 30.0 | 5.0 | 5.0 | 5.0 | 5.0 | 5.0 |
| B' | — | — | — | — | — | — | — | — | — | — |
| C' | — | — | — | — | — | — | — | — | — | — |
| D' | — | — | — | — | — | — | — | — | — | — |
| E' | 96.95 | 96.9 | 92.0 | 87.0 | 66.0 | 93.9 | 92.0 | 92.0 | 92.0 | 92.0 |
| F' | 2.0 | 2.0 | 2.0 | 2.0 | 3.0 | 0.1 | — | — | 1.0 | 1.0 |
| G' | — | — | — | — | — | — | 2.0 | — | 1.0 | — |

TABLE 2-continued

| | | | | | | | | | | |
|---|---|---|---|---|---|---|---|---|---|---|
| H' | — | — | — | — | — | — | — | 2.0 | — | 1.0 |
| I' | 1.0 | 1.0 | 1.0 | 1.0 | 1.0 | 1.0 | 1.0 | 1.0 | 1.0 | 1.0 |
| J' | — | — | — | — | — | — | — | — | — | — |
| (1) | ⊚ | ⊚ | ⊚ | ⊚ | ⊚ | ○ | ⊚ | ⊚ | ⊚ | ⊚ |
| (2) | x | Δ | ○ | ○ | ○ | Δ | ○ | ○ | ○ | ⊚ |
| (3) | x | Δ | ○ | ○ | ○ | Δ | ○ | ○ | ○ | ⊚ |
| (4) | ⊚ | ⊚ | ⊚ | ⊚ | ⊚ | ⊚ | ⊚ | ⊚ | ⊚ | ⊚ |

| | Example | | | Comparative Example | | |
|---|---|---|---|---|---|---|
| Composition | 27 | 28 | 29 | 4 | 5 | 6 |
| A' | 5.0 | 5.0 | 5.0 | 5.0 | 5.0 | — |
| B' | — | — | — | — | 5.0 | — |
| C' | — | 5.0 | — | — | — | — |
| D' | — | — | 5.0 | — | — | — |
| E' | 92.0 | 87.0 | 87.0 | 94.0 | 92.0 | 92.0 |
| F' | — | 2.0 | 1.0 | — | — | 2.0 |
| G' | 1.0 | — | 1.0 | — | — | — |
| H' | 1.0 | — | — | — | — | — |
| I' | 1.0 | 1.0 | 1.0 | 1.0 | 1.0 | 1.0 |
| J' | — | — | — | — | 2.0 | — |
| (1) | ⊚ | ⊚ | ⊚ | Δ | x | ⊚ |
| (2) | ⊚ | ⊚ | ⊚ | Δ | Δ | Δ |
| (3) | ⊚ | ⊚ | ⊚ | Δ | Δ | Δ |
| (4) | ⊚ | ⊚ | ⊚ | Δ | Δ | Δ | wherein, in Table 2,

Powder Portion

A': Silver ion, zinc ion, and ammonium ion carrying zeolite (Zeomic AJ10D made by Shinanen Zeomic, average particle size about 1.5 μm)

B': Silver ion carrying zeolite (average particle size about 1.5 μm)

C': Aluminum hydroxychloride

D': Zinc oxide

E': Talc

Oil Component

F': Dimethyl polysiloxane

G': Decamethylhexacyclosiloxane

H': Polyether modified dimethyl polysiloxane (POE content 20%, viscosity 500 cst/25° C.)

I': Synthetic isoparaffin

J': Isopropyl myristate (1): Useability (free from roughness)

(2): Odor (underarm odor)

(3): Odor (foot odor)

(4): Resistance to discoloration

Examples 30 to 43 and Comparative Examples 7 to 8

Deodorant Sticks

The deodorant sticks of Examples 30 to 43 and Comparative Examples 7 and 8 shown in Table 3 were prepared and evaluated as to useability (lack of roughness), deodorizing effect (underarm odor), and resistance to discoloration. The results are shown.

Manufacturing Process

The oil component and the dispersant were heated to melt and mixed, then added to a powder portion mixed separately by a Henschel mixer. The mixture was then filled in a container to obtain the deodorant stick.

Method of Evaluation (1) Useability

Twenty test subjects applied the deodorant sticks of the examples and the deodorant sticks of the comparative examples on either their left or right armpits and evaluated the feeling of use organoleptically by themselves.

Criterion of Evaluation

⊚: 18 to 20 subjects obtained non-rough feeling
○: 15 to 17 subjects obtained non-rough feeling
Δ: 10 to 14 subjects obtained non-rough feeling
x: 5 to 9 subjects obtained non-rough feeling
xx: 0 to 4 subjects obtained non-rough feeling The (2) deodorizing effect (underarm odor) and (3) resistance to discoloration were performed the same way as with Examples 1 to 16.

TABLE 3

| | Example | | | | | | | | | |
|---|---|---|---|---|---|---|---|---|---|---|
| Composition | 30 | 31 | 32 | 33 | 34 | 35 | 36 | 37 | 38 | 39 |
| A" | 0.05 | 0.1 | 5.0 | 10.0 | 30.0 | 5.0 | 5.0 | 5.0 | 5.0 | 5.0 |
| B" | — | — | — | — | — | — | — | — | — | — |
| C" | — | — | — | — | — | — | — | — | — | — |
| D" | — | — | — | — | — | — | — | — | — | — |
| E" | 30.0 | 30.0 | 30.0 | 20.0 | 10.0 | 30.0 | 30.0 | 30.0 | 30.0 | 30.0 |
| F" | 10.0 | 10.0 | 10.0 | 10.0 | 10.0 | 1.0 | 1.0 | 5.0 | — | — |

TABLE 3-continued

| | | | | | | | | | | |
|---|---|---|---|---|---|---|---|---|---|---|
| G" | — | — | — | — | — | — | — | — | 10.0 | — |
| H" | 20.0 | 20.0 | 20.0 | 20.0 | 20.0 | 25.0 | 25.0 | 25.0 | 20.0 | 20.0 |
| I" | 8.0 | 8.0 | 8.0 | 8.0 | 8.0 | 8.0 | 8.0 | 8.0 | 8.0 | 8.0 |
| J" | 30.95 | 30.9 | 26.0 | 31.0 | 21.0 | 30.9 | 30.0 | 26.0 | 26.0 | 26.0 |
| K" | — | — | — | — | — | — | — | — | — | 10.0 |
| L" | 1.0 | 1.0 | 1.0 | 1.0 | 1.0 | 1.0 | 1.0 | 1.0 | 1.0 | 1.0 |
| (1) | ⊙ | ⊙ | ⊙ | ⊙ | ⊙ | ○ | ⊙ | ⊙ | ⊙ | ⊙ |
| (2) | x | Δ | ○ | ○ | ○ | Δ | ○ | ○ | ○ | ○ |
| (3) | ⊙ | ⊙ | ⊙ | ⊙ | ⊙ | ⊙ | ⊙ | ⊙ | ⊙ | ⊙ |

| | Example | | | | Comparative Example | |
|---|---|---|---|---|---|---|
| Composition | 40 | 41 | 42 | 43 | 7 | 8 |
| A" | 5.0 | 5.0 | 5.0 | 5.0 | 5.0 | — |
| B" | — | — | — | — | — | 5.0 |
| C" | — | — | 15.0 | — | — | — |
| D" | — | — | — | 15.0 | — | — |
| E" | 30.0 | 30.0 | 15.0 | 15.0 | 30.0 | 30.0 |
| F" | 5.0 | 5.0 | 10.0 | — | — | 10.0 |
| G" | — | 5.0 | — | 10.0 | — | — |
| H" | 20.0 | 20.0 | 20.0 | 20.0 | 25.0 | 20.0 |
| I" | 8.0 | 8.0 | 8.0 | 8.0 | 8.0 | 8.0 |
| J" | 26.0 | 26.0 | 26.0 | 26.0 | 31.0 | 26.0 |
| K" | 5.0 | — | — | — | — | — |
| L" | 1.0 | 1.0 | 1.0 | 1.0 | 1.0 | 1.0 |
| (1) | ⊙ | ⊙ | ⊙ | ⊙ | x | ⊙ |
| (2) | ⊙ | ⊙ | ⊙ | ⊙ | Δ | Δ |
| (3) | ⊙ | ⊙ | ⊙ | ⊙ | Δ | x | wherein, in Table 3,

Powder Portion

A": Silver ion, zinc ion, and ammonium ion carrying zeolite (Zeomix AJ10D made by Shinanen Zeomix, average particle size about 1.5 μm)

B": Silver ion and zinc ion carrying zeolite (average particle size about 1.5 μm)

C": Aluminum hydroxychloride

D": Zinc oxide

E": Talc

Oil Component

F": Dimethyl polysiloxane

G": Octamethylcyclotetrasiloxane

H": Solid paraffin wax

I": Stearyl alcohol

J": Liquid paraffin

K": Polyether modified dimethyl polysiloxane

L": Sorbitan aliphatic acid ester (POE content 20%, viscosity 500 cst/25° C.)

(1): Useabiity (lack of roughness)
(2): Odor (underarm odor)
(3): Resistance to discoloration

Example 49

Pressed Powder Deodorant Cosmetic Composition

| (Powder Portion) | |
|---|---|
| Silver and ammonium ion carrying zeolite (average particle size about 3 μm) | 4.0 wt % |
| Aluminum hydroxychloride | 2.0 |
| Zinc oxide | 3.0 |
| Talc | 87.0 |
| (Oil Component) | |
| Methylphenyl polysiloxane | 3.0 |
| Liquid paraffin | 1.0 |
| (Additives) | |
| Perfume | q.s. |

The powder portion was mixed by a Henschel mixer, the oil component and additives were added to the mixture, then the result was pulverized by a 5HP Pulverizer (made by Hosokawa Micron). The result was press molded in a dish to obtain a pressed powder deodorant cosmetic composition.

The obtained pressed powder deodorant cosmetic composition was free of caking during use, the useability (lack of roughness) was excellent, and the deodorizing effect and resistance to discoloration were sufficient as well.

Example 50

Deodorant Powder

| | |
|---|---|
| Aluminum hydroxychloride | 13.0 wt % |
| Silver ion and aluminum ion carrying zeolite (average particle size 2 μm) | 7.0 |
| Spherical nylon powder | 5.0 |
| Dimethyl polysiloxane (molecular weight 450,000) | 1.0 |
| Synthetic paraffin | 1.0 |
| Perfume | q.s. |
| Talc | 73.0 |

Manufacturing Process

The above components were successively mixed by a Henschel mixer to obtain the deodorant powder. The obtained deodorant powder was superior in useability (lack of roughness), deodorizing effect, and resistance to discoloration.

Example 51

Powder Spray

| (Powder Portion) | |
|---|---|
| Aluminum hydroxychloride | 2.0 wt % |
| Silver ion, copper ion, and ammonium ion carrying zeolite (average particle size 1.5 μm) | 1.0 |
| Talc | 0.5 |
| (Oil Component) | |
| Decamethylcyclopentasiloxane | 1.5 |
| Perfume | 0.2 |
| (Propellants) | |
| Isopentane | 10.0 |
| Liquefied petroleum gas | 84.8 |

Manufacturing Process

The powder portion was mixed by a kneader, the oil component was mixed by a blender, and the both two were successively filled in a spray can. The propellants were then filled in the can to obtain the powder spray.

The obtained powder spray had a good dispersion of powder in the propellants, was free from clogging of the nozzle at the time of spraying, and was superior in deodorizing effect and resistance to discoloration.

Example 52

Powder Spray

| (Powder Portion) | |
|---|---|
| Silver ion, copper ion, and ammonium ion carrying zeolite (average particle size 5 μm) | 2.0 wt % |
| Zinc oxide | 0.2 |
| Silica | 1.5 |
| (Oil Component) | |
| Polyoxyethylene nonylphenylether | 0.5 |
| Dimethyl polysiloxane | 0.1 |
| Isopropyl myristate | 0.5 |
| (Additive) | |
| Polyoxyethylene sorbitan monooleate | 0.1 |
| Perfume | 0.1 |
| (Propellant) | 95.0 |
| Liquefied petroleum gas | 95.0 |

Manufacturing Process

The powder portion was mixed by a kneader, the oil component was mixed by a blender, the additives were added, and each was successively filled in a spray can. The propellant was then filled in the can to obtain the powder spray.

The obtained powder spray had a good dispersion of powder in the propellant, was free from clogging of the nozzle at the time of spraying, and was superior in deodorizing effect and resistance to discoloration.

Example 53

Compact-Shaped Deodorant Powder

| (Powder Portion) | |
|---|---|
| Copper ion, zinc ion, and ammonium ion carrying zeolite (average particle size about 1.5 μm) | 20.0 wt % |
| Talc | 60.0 |
| (Oil Component) | |
| Methylphenyl polysiloxane | 10.0 |
| Liquid paraffin | 10.0 |

Manufacturing Process

The powder portion was mixed by a Henschel mixer, the oil component was added to the mixture, then the result was pulverized by a 5HP pulverizer (made by Hosokawa Micron). The result was press molded in a dish to obtain a compact-shaped deodorant powder.

The obtained compact-shaped deodorant powder was sufficient in the useability (free from roughness), deodorizing effect, and resistance to discoloration.

Example 54

Deodorant Spray

| (Powder Portion) | |
|---|---|
| Zinc ion and ammonium ion carrying zeolite (average particle size about 5 μm) | 3.0 wt % |
| Zinc oxide | 2.0 |
| (Oil Component) | 5.0 |
| Octamethyl cyclotetrasiloxane | |
| (Additives) | |
| Isopropyl myristate | 0.5 |
| Diglycerol sorbitan tetra-2-ethylhexanoate | 0.5 |
| (Propellants) | 0.5 |
| n-butane | 76.0 |
| i-butane | 13.0 |

Manufacturing Process

The powder portion was mixed by a kneader, the oil component and additives were mixed by a blender, then these were successively filled in a spray can. The propellants were then added to obtain the deodorant spray.

The obtained deodorant spray was superior in dispersion of the powder in the propellants and was superior in useability (free from roughness), deodorizing effect, and resistance to discoloration.

Example 55

Baby Powder

| (Powder Portion) | |
|---|---|
| Talc | 80.3 wt % |
| Calcium carbonate | 17.0 |
| Silver ion and ammonium ion carrying | 2.0 |

-continued

| | |
|---|---|
| zeolite (average particle size about 8 μm) | |
| Methylphenyl polysiloxane | 0.4 |
| Dimethyl polysiloxane-polyethylene glycol copolymer (Additive) | 0.1 |
| Antiseptic | 0.2 |

Manufacturing Process

The above components were stirred and mixed well by a blender to obtain a baby powder.

The obtained baby powder was superior in the useability (free from roughness), deodorizing effect, and resistance to discoloration.

Example 56

Deodorant Stick

| | |
|---|---|
| Octamethylcyclotetrasiloxane | 60.0 wt % |
| Squalane | 10.0 |
| Hydrocarbon wax | 10.0 |
| Aluminum hydroxychloride | 5.0 |
| Zinc ion and ammonium ion carrying zeolite (average particle size about 10 μm) | 15.0 |

Manufacturing Process

The above components were mixed and filled in a container to obtain the deodorant stick.

The obtained deodorant stick was applied to the underarms and found to be superior in useability (free from roughness) and deodorizing effect and resistance to discoloration.

Example 57

Roll-On Deodorant

| | |
|---|---|
| Octamethylcyclotetrasiloxane | 67.0 wt % |
| Ethanol | 20.0 |
| Sorbitol | 4.0 |
| Aluminum hydroxychloride | 2.0 |
| Magnesium oxide | 2.0 |
| Silver ion, copper ion, and ammonium ion carrying zeolite (average particle size about 2 μm) | 5.0 |

Manufacturing Process

The above components were mixed and placed in a roll-on container to obtain a roll-on deodorant cosmetic composition.

The obtained roll-on deodorant cosmetic composition was free from aggregation of the particles and was superior in useability (free from roughness), deodorizing effect, and resistance to discoloration.

Example 58

Powder Spray

| | |
|---|---|
| (Powder Portion) | |
| Aluminum hydroxychloride | 2.0 wt % |
| Zinc ion, copper ion, and ammonium ion carrying zeolite (average particle size about 1.5 μm) | 1.0 |
| Talc | 0.5 |
| (Oil Component) | |
| Decamethylcyclopentasiloxane | 1.5 |
| Perfume | 0.2 |
| (Propellants) | |
| Isopentane | 10.0 |
| Liquefied petroleum gas | 84.8 |

Manufacturing Process

The powder portion was mixed by a kneader, the oil component was mixed by a blender, and the two were successively filled in a spray can. The propellants were then filled to obtain the powder spray.

The obtained powder spray was excellent is dispersion of the powder in the propellants, was free from clogging of the nozzle at the time of spraying, was excellent in spreadability on the skin, and was superior in sweat suppression, deodorizing effect, and resistance to discoloration.

Example 59

Powder Spray

| | |
|---|---|
| (Powder Portion) | |
| Silver ion, copper ion, and ammonium (average particle size about 1.0 μm) | 2.0 wt % |
| Zinc oxide | 0.2 |
| Silica | 1.5 |
| (Oil Component) | |
| Polyoxyethylene nonylphenylether | 0.5 |
| Dimethyl polysiloxane | 0.1 |
| Isopropyl myristate | 0.5 |
| (Additives) | |
| Polyoxyethylene sorbitan monooleate | 0.1 |
| Perfume | 0.1 |
| (Propellant) | 95.0 |
| Liquefied petroleum gas | |

Manufacturing Process

The powder portion was mixed in a kneader, the oil component was mixed in a blender, and the two were successively filled in a spray can. The propellant was then filled to obtain the powder spray.

The obtained powder spray was free from aggregation of the particle portion even with long term storage and was excellent in feeling of use and sufficient in deodorizing effect and resistance to discoloration as well.

Example 60

25 Compact-Shaped Deodorant Powder

| (Powder Portion) | |
|---|---|
| Silver ion, zinc ion, and ammonium ion carrying zeolite (average particle size about 1.5 µm) | 20.0 wt % |
| Talc | 60.0 |
| (Oil Component) | |
| Methyphenyl polysiloxane | 10.0 |
| Liquid paraffin | 10.0 |

Manufacturing Process

The powder portion was mixed by a Henschel mixer, the oil component was added to this mixture, then the result was pulverized by a 5HP pulverizer (Hosokawa Micron). The result was press molded in a dish to obtain a compact-shaped deodorant powder.

The obtained compact-shaped deodorant powder was free from caking during use, was excellent in feel of use on the skin, and was sufficient in deodorizing effect and resistance to discoloration as well.

Example 61

Deodorant Spray

| (Propellants) | |
|---|---|
| n-butane | 76.0 wt % |
| i-butane | 15.0 |
| (Oil Component) | 5.0 |
| Dimethyl polysiloxane | |
| (Powder Portion) | |
| Zinc ion and ammonium ion carrying zeolite (average particle size about 0.5 µm) | 3.0 |
| (Additives) | |
| Isopropyl myristate | 0.5 |
| Diglycerol sorbitan tetra-2-ethylhexanoate | 0.5 |

Manufacturing Process

The powder portion was mixed by a kneader, the oil component and the additives were mixed by a blender, then the two were filled in a spray can and the propellants were filled to obtain the deodorant spray.

The obtained deodorant spray had excellent dispersion of the powder portion in the propellants and when applied had a smooth, good feeling. The deodorizing effect and resistance to discoloration were also sufficiently exhibited.

Example 62

Baby Powder

| (Powder Portion) | |
|---|---|
| Talc | 80.0 wt % |
| Potassium carbonate | 17.0 |
| Silver ion, copper ion, and ammonium ion carrying zeolite (average particle size about 8 µm) | 2.0 |
| (Oil Component) | |
| Methylphenyl polysiloxane | 0.4 |
| Dimethyl polysiloxane-polyethylene glycol copolymer | 0.1 |
| (Additives) | |
| Antiseptic | 0.2 |

Manufacturing Process

The above components were stirred and mixed well by a blender to obtain the baby powder.

The obtained baby powder was free from aggregation, had a smooth feel of use, and was superior in deodorizing effect and resistance to discoloration.

Example 63

Deodorant Stick

| | |
|---|---|
| Octamethylcyclotetrasiloxane | 60.0 wt % |
| Squalane | 10.0 |
| Hydrocarbon wax | 10.0 |
| Silver ion, copper ion, zinc ion, and ammonium ion carrying zeolite (average particle size about 1.5 µm) | 20.0 |

Manufacturing Process

The above components were mixed and then filled in a container to obtain the deodorant stick.

The obtained deodorant stick had a smooth, good feel when it was applied to the underarm and was excellent in deodorizing effect and resistance to discoloration.

Example 64

Roll-On Deodorant Cosmetic Composition

| | |
|---|---|
| Octamethylcyclotetrasiloxane | 71.0 wt % |
| Ethanol | 20.0 |
| Sorbitol | 4.0 |
| Silver ion and ammonium ion carrying zeolite (average particle size about 10 µm) | 5.0 |

Manufacturing Process

The above components were mixed and placed in a roll-on container to prepare a roll-on deodorant cosmetic composition.

The obtained roll-on deodorant cosmetic composition was free from aggregation of the powder, had a fresh feel of use, was smooth to the skin, and was superior in deodorizing effect and resistance to discoloration.

Example 65

Body Cleanser

| | |
|---|---|
| Triethanolamine N-lauryl-L-glutamate | 6.0 wt %* |
| Sodium N-laurylmethyltaurate | 3.0 |
| Triethanolamine laurate | 9.5 |
| Triethanolamine myristate | 9.5 |
| Laurylimidazolium betaine | 5.0 |
| Lauryldiethanol amide | 5.0 |
| Propylene glycol | 7.0 |
| Silver ion and ammonium ion carrying zeolite (average particle size about 5 μm) | 0.5 |
| Methylphenyl polysiloxane | 1.0 |
| Purified water | 53.38 |
| Perfume | 0.01 |
| Antiseptic | 0.1 |
| Ethylenediaminetetraacetic acid | 0.01 |

Manufacturing Process

Purified water was heated to 70° C., the other components were successively added, and the mixture was stirred to dissolve. It was then cooled to ordinary temperature, then filled in a plastic bottle with agitation balls to obtain the body cleanser.

The above-mentioned body cleanser had cleansing ability and foaming ability and yet was excellent in the stabiity of the system and useability (free from roughness) and, further, was superior in deodorizing effect and resistance to discoloration.

Example 66

Calamine Lotion

| | |
|---|---|
| Ethanol | 13.0 wt % |
| (Oil Component) Octomoethylcyclotetrasiloxane | 2.0 |
| (Moisture Retainers) | |
| Glycerine | 2.0 |
| 1,3-butylene glycol | 2.0 |
| (Powder Agents) | |
| Iron oxide (red iron oxide) | 0.15 |
| Zinc oxide | 0.5 |
| Silver ion and ammonium ion carrying zeolite (average particle size about 1.5 μm) | 0.5 |
| Kaolin | 1.5 |
| (Medicines) | |
| Camphor | 0.2 |
| Phenol | 0.02 |
| Perfume | 0.01 |
| Color fading preventative | 0.01 |
| Purified water | 78.11 |

Manufacturing Process

The perfume was added to the ethanol, humectant and oil component and dissolved. The camphor and phenol were dissolved in the refined water and then the powder agents, color fading preventative, and above-mentioned ethanol-humectant phase were added and the mixture stirred to disperse the powder agents in a moist state. The mixture was filtered by an about 160 mesh filter to obtain the calamine lotion.

The above calamine lotion had the effect of soothing the burning sensation of the skin after sunburns and was superior in the useability, that is, free from roughness, deodorizing effect, and resistance to discoloration.

Example 67

Essence Oil

| | |
|---|---|
| (Oil Component) | |
| Olive oil | 49.69 wt % |
| Liquid paraffin | 25.0 |
| Squalane | 20.0 |
| (Powder) | |
| Simethyl polysiloxane | 3.0 |
| Silver ion, zinc ion, and ammonium ion carrying zeolite (average particle size about 5 μm) | 2.0 |
| (Others) | |
| Vitamin E acetate | 0.2 |
| Antioxidant | 0.1 |
| Perfume | 0.01 |

Manufacturing Process

The powder chemicals, antioxidant, and perfume were added to the oil component and stirred to obtain an oil which was then filled in a plastic bottle with agitation balls to obtain the essence oil.

The above-mentioned essence oil was superior in useability (free from roughness), deodorizing effect, and resistance to discoloration.

Example 68

Facial Cleanser

| | |
|---|---|
| (Aliphatic Acids) | |
| Stearic acid | 10.0 wt % |
| Palmitic acid | 10.0 |
| Myristic acid | 10.0 |
| Lauric acid | 4.0 |
| (Oil COmponent) | 2.0 |
| Methylphenyl polysiloxane | |
| (Alkali) | 6.0 |
| Potassium hydroxie | |
| (Humectant) | |
| PEG 1500 | 10.0 |
| Glycerine | 15.0 |
| Glycerol monostearic acid ester | 2.0 |
| POE (20) sorbitan monostearic acid (powder) | 2.0 |
| Silver ion and ammonium ion carrying zeolite (average particle size about 10 μm) | 2.0 |
| Antiseptic | 0.1 |
| Ethylene diaminetetraacetic acid | 0.05 |
| Perfume | 0.01 |
| Purified water | 26.84 |

Manufacturing Process

The aliphatic acids, oil component, humectant, and antiseptic were heated to dissolve and held at 70° C. Purified water in which the alkali had bee dissolved in advance was added in the oil phase while stirring. After the addition, the mixture was held at 70° C. to cause the neutralization reaction to end. Next, the melted surfactants, chelating agent, perfume, and powder were added and the mixture then stirred to mix it, then was deaerated, filtered, and cooled to obtain the facial cleanser.

Results of Evaluation

The above-mentioned facial cleanser was superior in useability (lack of roughness), deodorizing effect, and resistance to discoloration.

Example 69

Pack (Peel-Off Type)

| (Coating Agent) | |
| --- | --- |
| Polyvinyl acetate emulsion | 15.0 wt % |
| Polyvinyl alcohol | 10.0 |
| (Moisture Retainers) | |
| Sorbitol | 5.0 |
| PEG400 | 5.0 |
| (Oil Component) | |
| Jojoba oil | 2.0 |
| Methylphenyl polysiloxane | 1.0 |
| Squalane | 1.0 |
| (Surfactant) | 1.0 |
| POE sorbitan monostearic acid ester | |
| (Powders) | |
| Titanium oxide | 5.0 |
| Silver ion and ammonium ion carrying zeolite | 3.0 |
| (average particle size about 1.5 μm) | |
| Talc | 7.0 |
| (Alcohol) | |
| Ethanol | 8.0 |
| Perfume | 0.01 |
| Antiseptic | 0.1 |
| Purified water | 36.89 |

Manufacturing Process

The powders were added to the purified water to sufficiently disperse them, then the humectant were added. The mixture was heated to 70° to 80° C. then the coating agent was added and dissolved. The perfume, antiseptic, surfactant, and oil component were added to the ethanol. The mixture was then added to the above-mentioned water phase and mixed. The result was deaerated, filtered, and cooled to obtain a pack.

Results of Evaluation

The above-mentioned pack was superior in useability (free from roughness), deodorizing effect, and resistance to discoloration.

Example 70

Pressed Powder

| (Powders) | |
| --- | --- |
| Aluminum hydroxychloride | 5.0 wt % |
| Silver ion, zinc ion, and ammonium ion carrying zeolite | 5.0 |
| (average particle size about 6 μm) | |
| Talc | 87.0 |
| (Oil Component) | |
| Liquid paraffin | 2.0 |
| Methylphenyl polysiloxane | 1.0 |
| Perfume | q.s. |

Manufacturing Process

The powder component was sufficiently mixed, then the perfume, dissolved in the oil component, was sprayed uniformly and the result mixed. The powder was pulverized, then compression molded to obtain a pressed powder.

Results of Evaluation

The above-mentioned pressed powder was superior in useability (free from roughness), deodorizing effect, and resistance to discoloration.

Example 71

Soap

| | |
| --- | --- |
| Sodium lauryl monoglyceride sulfate | 54.87 wt % |
| Sodium lauryl sulfate | 10.0 |
| Sodium cocate | 30.0 |
| Cetyl alcohol | 3.5 |
| Methylphenyl polysiloxane | 0.5 |
| Silver ion and ammonium ion carrying zeolite | 1.0 |
| (average particle size about 1.5 μm) | |
| Perfume | 0.01 |
| Dye | 0.01 |
| Antioxidant | 0.1 |
| Ethylenediaminetetraacetic acid | 0.01 |

Manufacturing Process

The above components were added to a mixer and mixed and stirred, then the result was applied to a roll and plotter to squeeze and compress it to shape and extrude it in a bar shape. This was cut to obtain soap.

Results of Evaluation

The above-mentioned soap was superior in useability (free from roughness), deodorizing effect, and resistance to discoloration.

Example 72

Emollient Lotion

| (Oil Component) | |
| --- | --- |
| Cetyl alcohol | 1.0 wt % |
| Beeswax | 0.5 |
| Vaseline | 2.0 |
| Squalane | 6.0 |
| Dimethyl polysiloxane | 2.0 |
| (Alcohol) | |
| Ethanol | 5.0 |
| (Humectant) | |
| Vaseline | 4.0 |
| 1,3-butylene glycol | 4.0 |

-continued

| (Surfactant) | |
| --- | --- |
| POE (10) monooleic acid ester | 1.0 |
| Glycerol monostearic acid ester | 1.0 |
| (Mucilage) | |
| Quince seed extract (5% aqueous solution) | 20.0 |
| (Powder) | |
| Silver ion, copper ion, zinc ion, and ammonium ion carrying zeolite (average particle size 3.5 µm) | 2.0 |
| Antiseptic | 0.05 |
| Color | 0.01 |
| Perfume | 0.01 |
| Purified water | 51.43 |

Manufacturing Process

The moisture retainers and color agent were added to the purified water which was then heated to 70° C. The surfactants and antiseptic were added to the oil component which was then heated to 70° C. This was then added to the previous water phase and subjected to preliminary emulsion. The quince seed extract, powder, and ethanol were added to this and stirred. The emulsified particles were made uniform by a homogenizer, then the result was deaerated, filtered, and cooled to obtain the emollient lotion.

(Results of Evaluation)

The above-mentioned emollient lotion was superior in useability (lack of roughness), deodorizing effect, and resistance to discoloration.

Example 73

Oily Gel (Emusion Type)

| (Oil Component) | |
| --- | --- |
| Liquid paraffin | 10.0 wt % |
| Glycerol tri(2-ethylhexanoate) | 50.0 |
| Decamethylcyclopentasiloxane | 2.0 |
| (Humectant) | |
| Sorbitol | 10.0 |
| PEG 400 | 5.0 |
| (Surfactants) | |
| Acylmethyltaurine | 5.0 |
| POE octyldodecyl alcohol ester | 10.0 |
| (Powder) | |
| Silver ion, zinc ion, and ammonium ion carrying zeolite (average particle size about 2.0 µm) | 2.0 |
| Perfume | 0.01 |
| Purified water | 5.99 |

Manufacturing Process

The Humectant and acylmethyltaurine were added to the purified water which was then heated to 70° C. The POE octyldodecyl ether and perfume were added to the oil component which was then heated to 70° C. The powder was gradually added to the previous water phase. The emulsified particles were made uniform by a homogenizer, then the result was deaerated, filtered, and cooled to obtain an oily gel.

Results of Evaluation

The above-mentioned oily gel was superior in useability (lack of roughness), deodorizing effect, and resistance to discoloration.

Example 74

Cream

| (Oil Component) | |
| --- | --- |
| Cetyl alcohol | 5.0 wt % |
| Stearic acid | 3.0 |
| Methylphenyl polysiloxane | 1.0 |
| Vaseline | 4.0 |
| Squalane | 9.0 |
| Glyceryl tri(2-ethylhexanoic acid) | 7.0 |
| (Humectant) | |
| Dipropylene glycol | 5.0 |
| Glycerol | 5.0 |
| (Surfactants) | |
| Propylene glycol monostearic acid ester | 3.0 |
| POE (20) cetyl alcohol ether | 3.0 |
| (Alkali) | |
| Triethanol amine | 1.0 |
| (Powder) | |
| Silver ion and ammonium ion carrying zeolite (average particle size about 1.5 µm) | 1.0 |
| Antiseptic | 0.1* |
| Antioxidant | 0.05 |
| Perfume | 0.01 |
| Purified water | 52.84 |

Manufacturing Process

The humectant and alkali were added to purified water which was then heated to 70° C. The oil component was heated to melt, then the surfactants, antiseptic, antioxidant, and perfume were added and the result heated to 70° C. This was added to the prior water phase and the two were preliminarily emulsified. The powder was added and emulsified particles were made uniform by a homogenizer, then the mixture was deaerated, filtered, and cooled.

Results of Evaluation

The above-mentioned cream was superior in useability (lack of roughness), deodorizing effect, and resistance to discoloration.

According to the present invention, the dispersion of the powder becomes better, no aggregation occurs, and a superior useability (lack of roughness), deodorizing effect, and resistance to discoloration are obtained.

We claim:

1. A deodorant cosmetic composition superior in resistance to discoloration and dispersion comprising (i) an antibacterial zeolite, having at least a portion of its ion exchangeable ions substituted with ammonium ions and antibacterial metal ions, and (ii) silicone, blended together.

2. A deodorant cosmetic composition as claimed in claim 1, wherein the amount of the antibacterial zeolite blended is at least 0.1% by weight.

3. A deodorant cosmetic composition as claimed in claim 1, wherein the silicone is blended in an amount at least 1/10 that of the antibacterial zeolite by weight.

4. A deodorant cosmetic composition as claimed in claim 1, wherein the deodorant cosmetic composition is an aerosol.

5. A deodorant cosmetic composition as claimed in claim 4, wherein 0.1 to 70% by weight of the antibacterial zeolite and 0.01 to 80% by weight of silicone are blended.

6. A deodorant cosmetic composition as claimed in claim 5, wherein the amount of the antibacterial zeolite blended is at least 1.0% by weight.

7. A deodorant cosmetic composition as claimed in claim 1, wherein that the deodorant cosmetic composition is a stick.

8. A deodorant cosmetic composition as claimed in claim 7, wherein 0.1 to 70% by weight of the antibacterial zeolite and 0.01 to 80% of silicone are blended.

9. A deodorant cosmetic composition as claimed in claim 1, wherein the deodorant cosmetic composition is a powder.

10. A deodorant cosmetic composition as claimed in claim 9, wherein 0.1 to 99.99% by weight of the antibacterial zeolite and 0.01 to 10% by weight of silicone are blended.

11. A deodorant cosmetic composition as claimed in claim 1, wherein the deodorant cosmetic composition is a lotion.

12. A deodorant cosmetic composition as claimed in claim 11, wherein 0.1 to 20% of the antibacterial zeolite and 0.01 to 80% by weight of silicone are blended.

13. A deodorant cosmetic composition as claimed in claim 8, wherein the amount of the antibacterial zeolite blended is at least 5.0% by weight.

14. A deodorant cosmetic composition as claimed in claim 1, wherein the silicone is silicone oil and/or volatile silicone.

15. A deodorant cosmetic composition as claimed in claim 1, wherein the silicone is a dimethyl polysiloxane.

16. A deodorant cosmetic composition as claimed in claim 1, wherein the silicone is a methylphenyl polysiloxane.

17. A deodorant cosmetic composition as claimed in claim 1, wherein an aluminum compound is blended.

18. A deodorant cosmetic composition as claimed in claim 1, wherein a metal oxide is blended.

19. A deodorant cosmetic composition as claimed in claim 1, wherein the antibacterial metal ions are one or two or more types selected from the group consisting of silver, copper, zinc, mercury, tin, lead, bismuth, cadmium, chromium, and thallium.

20. A deodorant cosmetic composition as claimed in claim 1, wherein the antibacterial metal ions are one or two or more types selected from the group consisting of silver, copper, and zinc.

21. A deodorant cosmetic composition as claimed in claim 1, wherein the average particle size of the antibacterial zeolite is no more than 10 μm and in the range of particle size no more than 20% of the particles exceed a particle size of 1 μm.

22. A deodorant cosmetic composition as claimed in claim 2, wherein the deodorant cosmetic composition is an aerosol.

23. A deodorant cosmetic composition as claimed in claim 3, wherein the deodorant cosmetic composition is an aerosol.

24. A deodorant cosmetic composition as claimed in claim 2, wherein that the deodorant cosmetic composition is a stick.

25. A deodorant cosmetic composition as claimed in claim 3, wherein that the deodorant cosmetic composition is a stick.

26. A deodorant cosmetic composition as claimed in claim 2, wherein the deodorant cosmetic composition is a powder.

27. A deodorant cosmetic composition as claimed in claim 3, wherein the deodorant cosmetic composition is a powder.

28. A deodorant cosmetic composition as claimed in claim 2, wherein the deodorant cosmetic composition is a lotion.

29. A deodorant cosmetic composition as claimed in claim 3, wherein the deodorant cosmetic composition is a lotion.

30. A deodorant cosmetic composition as claimed in claim 10, wherein the amount of the antibacterial zeolite blended is at least 5.0% by weight.

31. A deodorant cosmetic composition as claimed in claim 12, wherein the amount of the antibacterial zeolite blended is at least 5.0% by weight.

* * * * *